United States Patent [19]
Stoner et al.

[11] Patent Number: 5,902,574
[45] Date of Patent: May 11, 1999

[54] SHAVING PREPARATION FOR IMPROVED SHAVING COMFORT

[75] Inventors: Karla Leum Stoner, Frederick; Charles W. Slife, Mount Airy, both of Md.

[73] Assignee: The Gillette Company, Boston, Mass.

[21] Appl. No.: 08/756,591

[22] Filed: Nov. 27, 1996

Related U.S. Application Data

[60] Continuation-in-part of application No. 08/584,765, Jan. 11, 1996, Pat. No. 5,665,340, which is a division of application No. 08/247,915, May 23, 1994, Pat. No. 5,500,210.

[51] Int. Cl.$^6$ ..................................................... A61K 7/15
[52] U.S. Cl. ..................... 424/73; 424/70.51; 424/70.22; 424/70.31; 424/45; 514/789; 514/944; 514/945
[58] Field of Search .......................... 424/73, 70.1, 70.51, 424/70.22, 70.31, 45

[56] References Cited

U.S. PATENT DOCUMENTS

| | | | |
|---|---|---|---|
| 3,708,431 | 1/1973 | Prussin | 424/73 |
| 3,728,356 | 4/1973 | Yablonski | 260/309 |
| 3,981,681 | 9/1976 | de la Guardia | 8/161 |
| 4,121,904 | 10/1978 | Schamper | 8/161 |
| 4,170,821 | 10/1979 | Booth | 30/41 |
| 4,618,344 | 10/1986 | Wells | 8/161 |
| 4,631,064 | 12/1986 | Juneja | 8/161 |
| 4,775,530 | 10/1988 | Perricone | 424/73 |
| 4,786,493 | 11/1988 | Smith et al. | 424/59 |
| 4,913,900 | 4/1990 | Kolc et al. | 424/72 |
| 4,935,231 | 6/1990 | Pigiet | 424/71 |
| 4,944,939 | 7/1990 | Moore | 424/73 |
| 4,982,750 | 1/1991 | Kaitz | 424/72 |
| 5,225,191 | 7/1993 | de Labbey | 424/71 |
| 5,382,426 | 1/1995 | Nandagiri | 424/70.51 |
| 5,387,412 | 2/1995 | Moore | 424/73 |
| 5,456,907 | 10/1995 | Nandagiri | 424/70.51 |
| 5,460,809 | 10/1995 | Nandagiri | 424/70.51 |
| 5,628,991 | 5/1997 | Samain et al. | 424/70.1 |

FOREIGN PATENT DOCUMENTS

| | | |
|---|---|---|
| 551135 | 7/1993 | European Pat. Off. . |
| 95/31960 | 11/1995 | WIPO . |

*Primary Examiner*—Thurman K. Page
*Assistant Examiner*—James M. Spear
*Attorney, Agent, or Firm*—Stephan P. Williams

[57] ABSTRACT

The present invention embraces a shaving composition comprising about 65 to 90% water, about 5 to 25% of a water-soluble surface active foaming agent, and about 0.2 to 2.3%, preferably about 0.3 to about 1.5%, and more preferably about 0.5 to about 1.0%, of cysteamine. Such a shaving composition provides improved shaving comfort when compared to a similar shaving composition without the reducing agent, particularly when utilized in conjunction with a humectant aftershave treatment.

16 Claims, No Drawings

SHAVING PREPARATION FOR IMPROVED SHAVING COMFORT

CROSS-REFERENCE TO RELATED APPLICATIONS

This application is a continuation-in-part of application Ser. No. 08/584,765 filed Jan. 11, 1996, U.S. 5,665,340 which is a division of application Ser. No. 08/247,915 filed May 23, 1994, now U.S. Pat. No. 5,500,210.

FIELD OF THE INVENTION

This invention relates to a method and composition for improving shaving comfort. More particularly, this invention relates to the sequential application of two compositions which combine to provide superior hair softening which results in reduced cutting forces, whereby a more comfortable shave is achieved.

BACKGROUND OF THE INVENTION

Experience and testing have shown that softening of the hair fiber prior to shaving is of paramount importance to achieving a comfortable shave. Normal applications of water and shaving preparations take three or more minutes to fully hydrate and soften the hair, thereby providing the least resistance to cutting and giving the most comfortable shave. However, the majority of shavers do not choose to wait that length of time and, on average, prepare their hair for one minute or less prior to shaving, leaving considerable room for improvements in comfort.

The major barrier to penetration of water and other materials into the hair is the cuticle, the hair's outermost layers of highly crosslinked keratin protein. It is known that reducing agents which break the sulfur to sulfur or disulfide bonds, that give hair its strength and rigidity, will modify this cuticle layer and increase the rate of water penetration into the hair after treatment. This can be shown through changes in tensile properties of hair, such as stress relaxation, yield stress and rate of water uptake in treated compared to non-treated hairs. It is believed that this breakage of disulfide bonds makes the hair more porous, allowing water to enter more easily and rapidly.

It is now well-known to utilize reducing agents for waving or straightening hair, and as depilating agents for removal of hair without shaving when used at higher concentrations and pH's. See, for example, Balsam and Sagarin, Cosmetics Science and Technology, vol. 2, pages 39–72 and 167–278 (2nd ed. 1972). The use of a reducing agent in a shaving cream or pre-shave lotion has been suggested in U.S. Pat. No. 3,728,356, U.S. Pat. No. 4,775,530 and U.S. Pat. No. 4,935,231 and the possibility of incorporating a depilatory agent in a cartridge razor lubricating strip has been mentioned in U.S. Pat. No. 4,170,821. Compositions containing a depilatory agent and a sodium soap to increase the speed of depilation have been disclosed in U.S. Pat. No. 4,121,904. It is also disclosed in U.S. Pat. No. 4,913,900 and EP 551,135 that moisturizing agents and humectants may be added to hair waving compositions containing reducing agents to reduce damage to the hair and improve softness.

SUMMARY OF THE INVENTION

The present invention comprises a method of improving shaving comfort by softening the hair to be shaved so as to reduce the cutting force required to cut it. The novel method comprises carrying out the following sequential steps:

(a) contacting an area of hair to be shaved with a reducing agent that breaks disulfide linkages in hair;

(b) contacting the area of hair treated in step (a) with a humectant and allowing it to dry or partially dry;

(c) contacting the area treated in step (b) with water to hydrate the hair; and (d) shaving the hydrated hair of step (c).

A preferred way of carrying out the method of the present invention comprises the following sequential steps:

(a) contacting an area of hair to be shaved with a reducing agent that breaks disulfide linkages in hair and water;

(b) shaving the area of hair treated in step (a);

(c) contacting the shaved area of step (b) with a humectant and allowing it to dry or partially dry; and (d) repeating steps (a), (b), and (c) at least once.

In carrying out the above method, the reducing agent is preferably included in a first dermatologically acceptable vehicle and the humectant is preferably included in a second dermatologically acceptable vehicle. The present invention also embraces a novel shaving system comprising in separate containers packaged for use in combination (a) a first dermatologically acceptable vehicle containing a reducing agent which is capable of breaking disulfide linkages in hair; and (b) a second dermatologically acceptable vehicle containing a humectant.

It has been discovered that the afore-described sequential application to the hair of a reducing agent followed by a humectant provides superior and rapid softening of the hair fiber upon rehydration prior to shaving, resulting in easier cutting of the hair, thereby providing a smoother, more comfortable shave. The two step pretreatment allows hair to hydrate and soften more quickly than untreated hair, hair treated with either agent alone, or hair treated with both agents simultaneously. Moreover, the two-step pretreatment provides for superior softening with reduced irritancy because the reducing agent can be effectively utilized at lower concentrations and less alkaline pH's when followed by the humectant. Thus, the present invention provides a more comfortable shave even with shorter preparation times.

The present invention additionally embraces a shaving composition comprising about 65 to 90% water, about 5 to 25% of a water-soluble surface active foaming agent, and about 0.2 to 2.3%, preferably about 0.3 to about 1.5%, and more preferably about 0.5 to about 1.0%, of cysteamine. Such a shaving composition provides improved shaving comfort when compared to a similar shaving composition without the reducing agent, particularly when utilized in conjunction with a humectant aftershave treatment as described above.

DETAILED DESCRIPTION OF THE INVENTION

Reducing agents which are capable of breaking disulfide bonds in hair keratin are well-known in the field of hair waving, hair straightening and hair depilation. Typical of such materials are the water soluble mercaptans such as thioglycolic acid, thiolactic acid, cysteine, cysteine ethyl ester, cysteine methyl ester, N-acetyl cysteine, cysteamine, thioglycerol, thioglycolic hydrazide, thioglycolamide, glycerol monothioglycolate, $\beta$-mercapto-propionic acid, N-hydroxyethyl-mercapto-acetamide, N-methyl-mercapto-acetamide, $\beta$-mercapto-ethylamine, $\beta$-mercaptopropionamide, 2-mercapto-ethane-sulfonic acid, $\alpha$-mercaptoethanol, 1,3-dithio-2-propanol, 1,4-dithio-2-butanol, 1,4-dimercapto-2-aminopropane, 1,4-dimercapto-2,3-diaminobutane, dimercaptoadipic acid, mercaptopropionic acid, dithiothreitol, homocysteinethiolactone, N-mercaptoalkylgluconamides, N-(mercaptoalkyl)-$\omega$-hydroxyalkylamides, thioglyceryl alkyl ethers, 1-phenyl 2-mercaptoethanol and salts of the aforementioned agents where appropriate, such as the ammonium, sodium, potassium, calcium, magnesium or mono- or diethanolamine salts, which are known to be active. Other known reducing agents include ammonium, sodium and potassium sulfites and bisulfites, sodium or potassium borohydride, barium sulfide and metal siliconates of the formula $R_a$—Si—$(O^- M^+)_{4-a}$ as described in U.S. Pat. No. 4,985,240. Of these, the preferred reducing agents include the ammonium, sodium, potassium, calcium, magnesium and mono- or diethanolamine salts of thioglycolic acid, cysteine, cysteamine, cysteine hydro- chloride, cysteine methyl ester, cysteine ethyl ester, N-acetyl cysteine, diammonium dithioglycolate, and the ammonium, sodium and potassium sulfites and bisulfites.

The most preferred reducing agent is cysteamine, which may be advantageously used at relatively low concentrations, typically from about 0.2 to about 2.3%, preferably about 0.3 to about 1.5%, and more preferably about 0.5 to about 1.0%, by weight in an aqueous liquid vehicle. At such low concentrations the odor is substantially reduced, while the shave comfort improving activity is retained. For optimum activity and minimum skin irritation, the pH of the composition containing the reducing agent (e.g. cysteamine) should be adjusted to about 8 to about 11, more preferably about 9 to about 10, and most preferably about 9.3 to 9.8.

The reducing agent, or a mixture of reducing agents, is preferably incorporated in a first dermatologically acceptable vehicle at a concentration which is sufficient to soften the protein structure of the hair without causing depilation or significant skin irritation. The concentration of the reducing agent will typically fall within the range of about 0.2 to 20% by weight depending upon the activity of the particular reducing agent employed. The pH of the vehicle should be adjusted to between 5 and 12.5 to balance optimum activity of the particular reducing agent employed versus skin irritancy, and should preferably fall between 6 and 10, more preferably about 9 to 10. The vehicle will preferably contain a substantial amount of water, most preferably about 60 to 98% by weight.

The vehicle containing the reducing agent may also include a wide variety of other optional components depending upon the form and characteristics of the vehicle which are desired. For example, it may include agents which are known to promote swelling of the hair and/or enhance penetration of the reducing agent such as, for example, urea, thiourea, guanidine, amino guanidine and biguanide. Such agents are typically present at concentrations ranging from about 0.1M to about 2.0M. The vehicle may also optionally include surfactants, fillers, gelling agents, thickeners, emollients, moisturizers, fragrances, coloring agents, and preservatives. However, ingredients which would tend to coat the hair and impede penetration of water and the reducing agent should generally be avoided. Such ingredients are typically hydrophobic and include various types of oils and fatty materials.

It is preferred that the vehicle containing the reducing agent is in the form of a cream, foam, lotion or gel, and most preferably a shaving cream, foam or gel. Such a formulation will typically comprise about 65 to 90%, preferably about 70 to 90%, water and about 5 to 25%, preferably about 10 to 20%, of a surface active foaming agent selected from one or more water-soluble soaps, anionic surfactants and non-ionic surfactants. Naturally, of course, the shaving formulation may contain a variety of well-known cosmetic ingredients which are typically used to enhance the performance attributes and aesthetics thereof.

A preferred shaving composition of the present invention comprises about 65 to 90% water, about 5 to 25% of a water-soluble surface active foaming agent, and about 0.2 to 2.3%, preferably about 0.3 to about 1.5%, and more preferably about 0.5 to about 1.0%, of cysteamine.

The water-soluble surface active foaming agent may comprise a water-soluble soap, an anionic surfactant, a non-ionic surfactant, or a mixture of one or more of these. Water-soluble soaps include, for example, the sodium, potassium and lower alkanolamine (preferably triethanolamine) salts of $C_{10}$ to $C_{20}$, preferably $C_{12}$ to $C_{18}$, fatty acids. Typical fatty acids include lauric, oleic, coconut oil, myristic, palmitic and stearic acid and mixtures thereof. For purposes of the present invention, the water- soluble soaps are also intended to include the interrupted soaps such as the sodium, potassium and lower alkanolamine (preferably triethanolamine) salts of N-fatty acyl sarcosines wherein the fatty acyl moiety has 10 to 20, preferably 12 to 18, carbon atoms. Typical sarcosines include stearoyl sarcosine, myristoyl sarcosine, palmitoyl sarcosine, oleoyl sarcosine, lauroyl sarcosine, cocoyl sarcosine and mixtures thereof. The soaps (including the interrupted soaps) may be utilized in preneutralized form (i.e. as the sodium, potassium or alkanolamine salt) or in the free acid form followed by subsequent neutralization with sodium hydroxide, potassium hydroxide and/or alkanolamine (preferably triethanolamine). In any event, the composition must contain sufficient base to neutralize the soap component and adjust the pH to the desired level, preferably about pH 9–10. Any suitable base may be used for this purpose, with sodium hydroxide, potassium hydroxide and triethanolamine being the most common. The base is typically present in an amount of about 1 to 7% by weight of the shaving composition.

It is generally desirable to include a non-ionic surfactant in the composition to improve foam quality, wettability, gel consistency, and/or rinsability. Suitable non-ionic surfactants will typically have an HLB of 14 or more and will generally be included in an amount up to about 8%, preferably about 1 to 6%, of the composition. Preferred non-ionic surfactants include the polyoxyethylene ethers of fatty alcohols, acids and amides, particularly those having 10 to 20, preferably 12 to 18, carbon atoms in the fatty moiety and about 8 to 60, preferably 10 to 30, ethylene oxide units. These include, for example, Oleth-20, Steareth-21, Ceteth-20, and Laureth-23. Other non-ionic surfactants include the polyoxyethylene ethers of alkyl substituted phenols, such as Nonoxynol-4 and Nonoxynol-20, fatty alkanolamides such as Lauramide DEA and Cocamide MEA, polyethoxylated sorbitan esters of fatty acids, such as Polysorbate-20, lauryl polyglucoside, sucrose laurate, and polyglycerol 8-oleate.

The shaving composition may also include one or more anionic surfactants. These include, for example, the sodium, potassium, ammonium and substituted ammonium salts (such as the mono-, di- and triethanolamine salts) of $C_8$–$C_{22}$, preferably $C_{12}$–$C_{18}$, alkyl sulfates (e.g. sodium lauryl sulfate, ammonium lauryl sulfate), alkyl sulfonates (e.g. ammonium lauryl sulfonate), alkylbenzene sulfonates (e.g. ammonium xylene sulfonate), acyl isethionates (e.g. sodium cocoyl isethionate), acyllactylates (e.g. sodium cocoyl lactylate) and alkyl ether sulfates (e.g. ammonium laureth sulfate).

In addition to the surface active foaming agent, the shaving composition may include a variety of other well-known cosmetic ingredients generally known for use in shaving creams, foams and gels to improve the aesthetics and performance characteristics of the composition.

The shaving composition may contain about 1 to 10%, preferably about 1.5 to 7%, of a non-volatile paraffinic hydrocarbon fluid. The terms "non-volatile" and "fluid" mean that these materials are liquid at room temperature and have a boiling point above 200° C. Such hydrocarbon fluids include mineral oils and branched-chain aliphatic liquids. These fluids typically have from about 16 to about 48, preferably about 20 to about 40, carbon atoms and a viscosity of about 5 to about 100 cs., preferably about 10 to about 50 cs., at 40° C. The preferred non-volatile paraffinic hydrocarbon fluid is selected from mineral oil with a viscosity of about 10 to about 50 cs. at 40° C., hydrogenated polyisobutene with a molecular weight of about 320 to about 420, and mixtures thereof.

It may also be desirable to include a water-soluble gelling aid or thickening agent in the shaving composition to improve its consistency and stability, as well as to adjust its viscosity. These may include, for example, hydroxyalkyl cellulose polymers such as hydroxyethyl cellulose and hydroxypropyl cellulose (sold under the trademarks "Natrosol" and "Klucel" respectively), copolymers of acrylic acid and polyallyl sucrose (sold under the trademark "Carbopol"), carboxymethyl cellulose, and cellulose methyl ether (sold under the trademark "Methocel"). Natural or synthetic gums, resins, and starches may also be used. The preferred thickening agents are hydroxyethyl cellulose, hydroxypropyl cellulose, and mixtures thereof. The gelling aid or thickening agent is typically included in an amount of about 0.01 to 5%, preferably about 0.1 to 2%, by weight of the composition.

The shaving composition may also include up to 8%, preferably about 2 to 6%, by weight of a fatty alcohol such as myristyl, lauryl and stearyl alcohol and octyl dodecanol. The term "fatty" is intended to include 10 to 20, preferably 12 to 18, carbon atoms.

It may also be advantageous to include in the composition a cationic conditioning polymer which is substantive to the skin in order to improve lubricity and post-shave skin feel. Such polymers may include polymeric quaternary ammonium salts of hydroxyethyl cellulose such as polyquaternium-10 and polyquaternium-24. These polymers are typically included in an amount of about 0.05 to 2%, preferably about 0.1 to 1%, by weight.

Other useful additives which may be utilized in the composition include humectants such as glycerin, sorbitol, and propylene glycol, emollients including fatty esters such as isopropyl myristate, decyl oleate, 2-ethylhexyl palmitate, PEG-7 glyceryl cocoate, and glyceryl linoleate, propoxylated fatty ethers such as PPG-10 cetyl ether and PPG-11 stearyl ether, di- and triglycerides such as lecithin and caprylic/capric triglyceride, vegetable oils, and similar materials, skin freshening and soothing agents such as menthol, aloe, allantoin, lanolin, collagen and hyaluronic acid, lubricants such as polyethylene oxide, fluorosurfactants, and silicones ( e.g. dimethicone, dimethiconol, dimethicone copolyol, stearyl dimethicone, cetyl dimethicone copolyol, phenyl dimethicone, cyclomethicone, etc.), vitamins (including vitamin precursors and derivatives) such as panthenol, vitamin E, tocopherol acetate, and vitamin A palmitate, colorants, fragrances, antioxidants and preservatives. As mentioned previously, however, the quantity of hydrophobic agents included in the composition should be adjusted to a sufficiently low level so as not to interfere with the action of the reducing agent on the hair.

If the shaving composition is in the form of a self-foaming shave gel, it will include a self-foaming agent which may be any volatile hydrocarbon with a sufficiently low boiling point that it will volatilize and foam the gel upon application to the skin, but not so low that it causes the gel to foam prematurely. The typical boiling point of such an agent generally falls within the range of 20 to 40° C. Preferred self-foaming agents are selected from saturated aliphatic hydrocarbons having 4 to 6 carbon atoms, such as n-pentane, isopentane, neopentane, n-butane, isobutane, and mixtures thereof. Most preferred is a mixture of isopentane and isobutane in a weight ratio of about 1:1 to about 3:1. The self-foaming agent will normally be present in an amount comprising about 1 to 8% of the composition, preferably about 2 to 5%.

If the shaving composition is in the form an aerosol foam, it will include a propellant of sufficient volatility or pressure to propel the shaving composition from its container and cause it to foam. Typical propellants include compressed air and more typically a volatile hydrocarbon or mixture of hydrocarbons (typically with 3 to 6 carbon atoms) having a vapor pressure of 30 to 60 psig at about 20° C. A preferred propellant has the industry designation A-46 and is a mixture of n-butane, isobutane and propane with a vapor pressure of 46 psig at about 20° C. When the propellant is a volatile hydrocarbon, it typically comprises about 1 to 5%, preferably about 2 to 4%, of the composition.

One type of shaving composition of the present invention is an aerosol shaving foam which comprises, in percent by weight, about 65 to 90% (preferably about 70 to 90%) water, about 4 to 20% (preferably about 6 to 16%) of a water-soluble soap, sufficient base to solubilize the soap and provide a pH of about 8 to 11 (preferably about 9–10), the reducing agent (preferably about 0.3–1.5% cysteamine), and propellant (preferably about 1 to 5% volatile hydrocarbon). The water-soluble soap is selected from the group consisting of fatty acid soap, N-fatty acyl sarcosine and mixtures thereof, wherein the fatty acid or fatty acyl have 10 to 20, preferably 12 to 18, carbon atoms. The base is selected from the group consisting of sodium hydroxide, potassium hydroxide, lower alkanolamine and mixtures thereof, with triethanolamine being preferred. The base generally comprises about 1 to 7% of the composition. Preferably the composition will also include about 1 to 6% of a non-ionic surfactant (e.g. Oleth-20, Laureth-23).

Another type of shaving composition of the present invention is a non-aerosol shave gel which comprises, in percent by weight, about 65 to 90% (preferably about 70 to 90%) water, about 4 to 20% (preferably about 6 to 16%) of a water-soluble soap, sufficient base to solubilize the soap and provide a pH of about 8 to 11 (preferably about 9–10), a water-soluble gelling agent, and the reducing agent (preferably 0.3–1.5% cysteamine). The soap and base are as described in the preceding paragraph. The gelling agent may be a polyethylene glycol polymer, such as Oleth-20, Laureth-23, or Poloxamer 407, or a thickener such as hydroxyethyl cellulose, hydroxypropyl cellulose, or copolymers of acrylic acid and polyallyl sucrose, or a mixture of any of these gelling agents. The gelling agent typically comprises about 0.1 to 6% of the composition.

A further type of shaving composition of the present invention is a self-foaming shave gel which comprises, in percent by weight, about 65 to 90%, (preferably about 70 to 90%) water, about 4 to 20% (preferably about 6 to 16%) of a water-soluble soap, sufficient base to solubilize the soap and provide a pH of about 8 to 11 (preferably about 9 to 10), a water-soluble gelling agent, the reducing agent (preferably 0.3–1.5% cysteamine), and about 1 to 8% self-foaming agent. The soap, base, gelling agent and self-foaming agent are as described above. In addition the composition may include about 1 to 10% non-volatile paraffinic hydrocarbon fluid and/or about 1 to 8% of a fatty alcohol.

The shaving compositions of the present invention may be packaged in any suitable dispenser normally used for dispensing shaving creams, foams or gels. These include aerosol dispensers in which the propellant is added to the same chamber as the shaving concentrate (e.g. as is typically done with shaving foams), aerosol dispensers with a barrier, such as a collapsible bag or piston, to separate the shaving concentrate from the propellant required for expulsion (e.g. as is typically done with post-foaming gels), collapsible tubes, and pump or squeeze containers. It is preferred to protect the composition from oxidation and heavy metal contamination. This can be achieved, for example, by purging the composition and container with nitrogen to remove oxygen and by utilizing inert containers (e.g. aluminum cans or polymer coated or lined cans).

A second part of the treatment method of the present invention comprises a humectant. Humectants are hygroscopic agents which are well-known in the cosmetic field. Suitable humectants are those which penetrate the hair and allow it to rehydrate quickly. The most common humectants are the polyhydric alcohols or polyhydroxy alkanes such as, for example, ethylene glycol, glycerin, propylene glycol, dipropylene glycol, triethylene glycol, 1,3-propanediol, butylene glycol, and sorbitol. Other suitable humectants include sodium pyroglutamate, N-acetyl-ethanolamine, sodium lactate, isopropanol, polyalkylene glycols of the formula

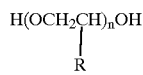

wherein R is H or $CH_3$ and n has an average value of about 2 to about 10, polyethylene glycol glyceryl ethers, and a variety of other ethoxylated and/or propoxylated chemical agents which are small enough to penetrate hair (e.g. molecular weight of 500 or less) and enhance its ability to rehydrate. Preferred humectants include glycerin, triethylene glycol, 1,3-propanediol, sodium pyroglutamate, sodium lactate, N-acetyl-ethanolamine and sorbitol.

The humectant, or a mixture of humectants, is preferably incorporated in a second dermatologically acceptable vehicle, generally at a concentration of about 5 to 50% by weight, preferably about 10–30%. The vehicle will preferably contain a substantial amount of water, generally from about 40 to about 90% by weight. The pH of the vehicle may be adjusted to suit the particular characteristics which are desired, but will preferably be approximately neutral (e.g. pH 5–8). The vehicle may contain a wide variety of other cosmetic ingredients depending upon the form and and characteristics of the vehicle which are desired. However, hydrophobic substances which might interfere with penetration of water and humectant into the hair should be avoided. The vehicle may include low to moderate amounts of alcohol as well as one or more agents known to swell hair.

It is preferred that the vehicle containing the humectant is in the form of an aftershave splash, lotion or gel. Such formulations will typically comprise about 20 to 80% water, about 0 to 50% ethyl alcohol, about 5–50% humectant, fragrance and optional thickening agent.

In a preferred method of practicing the present invention the first step will involve contacting the area of hair to be shaved with an aqueous shaving preparation, such as a conventional shaving cream or gel, which shaving preparation also contains a reducing agent. The area is then shaved and rinsed. The shaved area is then contacted with an aftershave preparation, such as an aftershave splash or gel, which contains a humectant which penetrates the shaved hair, allowing it to later rehydrate more quickly. When the hair in the shaved area has regrown and is ready to be shaved again, presumably the next day, it is hydrated by contacting it with water and preferably with the same or similar reducing-agent-containing shave preparation used in the first step. It may then be shaved again, rinsed, and the process repeated as many times as desired.

Since the advantage of the present invention is fully realized after both the reducing agent and humectant have been applied, it should be obvious that the second and subsequent shaves following the aforedescribed regimen will give the maximum benefit of increased smoothness and comfort over conventional shaving regimens. Naturally, since there are many ways of carrying out the treatment of the present invention, the invention is not limited to the aforedescribed technique, which merely represents one of the more practical embodiments thereof.

The invention may be further illustrated by reference to the following examples, in which all parts and percentages are by weight.

EXAMPLE 1

Facial beard hair was collected from men with 2 to 3 inches of beard growth which had not been treated with colorants, oxidizing or reducing agents or oily conditioners or regularly exposed to chemical fumes (e.g. professional painters) or sun. Hairs to be utilized in tests were preselected for pigmentation, 3 mil minor diameter (major diameter averaged 6 to 6.5 mils) and the presence of a consistent medulla in the fiber. Most tests utilized cheek fibers, but chin fibers may be used.

A small segment of beard hair was divided in half, with one half being treated as the test element and the other half as the control element. The test elements were immersed in a test material (aqueous reducing agent) for a set period of time (e.g. 3 min.) as indicated, and the control elements were likewise immersed in a control material (e.g. Foamy® shave cream). They were then removed, rinsed in running tap water for about 30 seconds and then immersed in the test material (humectant) or control material (e.g. water) for a set period of time (e.g. 3 min.). After removal, the hairs were allowed to air dry and equilibrate for a minimum of 18 hours at 70° F.±1° and 65%±2% relative humidity in a constant temperature and humidity room.

Cuts were made on a Free End Cutting Force Instrument, which utilizes a linear variable differential transformer configured as a load cell (similar to that used in a weighing balance) to detect the peak amount of force in grams required for a razor blade to cut through a beard hair. The hairs were cut in a free-end mount, that is the part of the hair to be cut is unsupported, and the blade cuts through the minor diameter, with the major diameter parallel to the blade edge. Test and control hairs were taped to small metal anvils for cutting and oriented such that cuts on the paired segments occur within a 1 mm distance on the original intact segment (i.e. before being divided into paired segments). Cuts made in this manner significantly reduced the effects of the normal high variability along the length of a beard fiber. Anvil mounted hairs were immersed in water or other hydrating material by inverting the anvil and supporting it over the container in such a way that all of the exposed hair and only a very small corner of the anvil was immersed. After about 55 seconds immersion, the anvil was immediately placed in the anvil holder on the cutting force instrument and the hair cut. The entire hydrating-cutting process was completed within about 65 seconds.

Data was calculated as the average of ratios of treated over control peak cutting forces for each pair of hairs. Ten to fourteen pairs were cut per test. The percent change (decrease or increase) in cutting force was calculated from the average of the ratios. The results of several tests are presented in Table 1.

TABLE 1

| | Treatment | Control | Decrease In Cutting Force |
|---|---|---|---|
| A | (1) 11.5% Cysteine pH 9.5 - 4 min. | Foamy Reg. | 14.5% |
| | (2) 25% aq. glycerin - 3 min. | Water | 23.5% |
| B | (1) 11.5% Cysteine pH 10.0 - 4 min. | Foamy Reg. | |
| | (2) 25% aq. glycerin - 3 min. | Water | |
| C | (1) 15.5% N-Acetyl Cysteine pH 10.0 - 4 min. | Foamy Reg. | 20.7% |
| | (2) 25% aq. glycerin - 3 min. | Water | |

TABLE 1-continued

| Treatment | | Control | Decrease In Cutting Force |
|---|---|---|---|
| D | (1) 8.2% N-Acetyl Cysteine pH 10.0 - 4 min. | Foamy Reg. | 11.2% |
|   | (2) 25% aq. glycerin - 3 min. | Water | |
| E | (1) 4.0% Ca Thioglycolate pH 9.5 - 4 min. | Foamy Reg. | 15.4% |
|   | (2) 25% aq. glycerin - 3 min. | Water | |
| F | (1) 3.3% NH$_3$ Thioglycolate pH 9.5 - 4 min. | 3.3% NH$_3$ Thioglycolate | 28.6% |
|   | (2) 25% aq. glycerin - 10 min. | Water | |
| G | (1) 15% Cysteine HCl pH 9.5 - 4 min. | Foamy Reg. | 11.0% |
|   | (2) 25% aq. glycerin - 3 min. | Water | |
| H | (1) 16.2% Cysteine methyl ester HCl pH 9.5 - 4 min. | Foamy Reg. | 21.0% |
|   | (2) 25% aq. glycerin - 3 min. | Water | |
| I | (1) 1.7% Cysteamine HCl pH 9.5 - 3 min. | Foamy Reg. | 10.2% |
|   | (2) 25% aq. glycerin - 3 min. | Water | |
| J | (1) Foamy Reg. - 10 min. | Foamy Reg. | none |
|   | (2) 25% aq. glycerin - 10 min. | Water | |

Example A was repeated but with the following humectants substituted for glycerin: triethylene glycol, 1,3-propanediol, pyroglutamic acid sodium salt, N-acetyl-ethanolamine, sodium lactate, sorbitol and ethylene glycol. The decrease in cutting force compared to the control ranged from 7 to 15%.

The above-described protocol was repeated using varying amounts of cysteamine as the reducing agent. The results are shown in Table 2.

TABLE 2

| Treatment | | Control | Decrease In Cutting Force |
|---|---|---|---|
| K | (1) 2.3% Cysteamine pH 9.5 - 4 min. | Foamy Reg. | 12.4% |
|   | (2) 25% aq. glycerin - 3 min. | Water | |
| L | (1) 1.2% Cysteamine pH 9.5 - 4 min. | Foamy Reg. | 11.8% |
|   | (2) 25% aq. glycerin - 3 min. | Water | |
| M | (1) 0.7% Cysteamine pH 9.5 - 4 min. | Foamy Reg. | 9.5% |
|   | (2) 25% aq. glycerin - 3 min. | Water | |
| N | (1) 0.7% Cysteamine pH 8.0 - 4 min. | Foamy Reg. | 6.6% |
|   | (2) 25% aq. glycerin - 3 min. | Water | |
| O | (1) 0.35% Cysteamine pH 9.5 - 4 min. | Foamy Reg. | 8.9% |
|   | (2) 25% aq. glycerin - 3 min. | Water | |

EXAMPLE 2

Panels of 8 to 10 men applied an aqueous solution of reducing agent to one side of their faces and water to the other side of their faces as a control. Both the reducing agent solution and the water were thickened to a thin gel with a water soluble hydroxyethylcellulose gum to permit the materials to remain on the face and to prevent them from drying out during the treatment time. One minute after application, panelists made three strokes with a twin blade razor in the central cheek area on each side of their faces and rated the sensation of pull on each side on a 10 point scale (0=no pull, 10=excessive pull). The test and control materials were then left on the face for an additional 2 to 3 minutes for a total treatment time of 3 to 4 minutes. The panelists then rinsed the materials off, applied a shave foam and completed shaving the rest of the face. After rinsing and drying the face, the same amount of aqueous humectant aftershave (25% glycerin) was applied to both sides of the face and remained on the face until the panelist washed his face later in the day. Panelists followed this procedure Monday through Friday of the first week of the study, used their regular shaving routine Saturday and Sunday, and continued with the same test procedure outlined for the first week during the second week, but with the sides of the face on which the reducing agent and water solutions were applied being switched. Panelists were not informed which sides of their face received the test and control materials. Using this test procedure, panelists have rated, on average, that the side of the face receiving the reducing agent/humectant application resulted in decreased pull compared to the control. The reducing agent solutions tested in this manner included cysteine (11.5%), N-acetyl cysteine (15.5%), Cysteamine HCl (1.0%) and NH$_3$ thioglycolate (3.3%).

EXAMPLE 3

| Aerosol shave foam | |
|---|---|
| Ingredient | Wt. % |
| Water | 83.27 |
| Stearic acid | 6.40 |
| Potassium hydroxide | 0.90 |
| Triethanolamine (99%) | 3.30 |
| Laureth-23 | 1.97 |
| Oleth-20 | 1.48 |
| Fragrance/preservative | 0.49 |
| Propellant A46 | 1.50 |
| Cysteamine | 0.69 |

Procedure: Charge deionized water to a mix tank and heat to 75° C., then add the stearic acid and mix until melted. Add pre-melted Laureth-23 and Oleth-20 and mix until blended, then add triethanolamine and mix the solution well for about thirty minutes. Add the preservative, cool the solution to about 30° C., add the fragrance and cysteamine and mix for about ten minutes, then adjust the pH to 9.5–9.7 with aqueous potassium hydroxide. Add the shaving concentrate to aerosol cans, purge the cans with nitrogen gas to remove oxygen, seal the cans, then add the propellant.

This shave foam composition was subjected to the cutting force analysis described in Example 1M, except that the post-treatment was Neutragena® Norwegian Formula® Emulsion (contains 20–25% glycerin and other ingredients) and the control was an identical shave foam without cysteamine. An 11.5% reduction in cutting force versus the control was demonstrated.

This shave foam composition was also tested in two split face shave studies with the control being an identical shave foam without cysteamine. In one study, no humectant aftershave was applied. In the other study, the above-mentioned Neutragena product was applied as an aftershave. In the first study (no aftershave), the shave foam with cysteamine provided directional improvement in pull and significant improvement in glide, during shave comfort, post shave closeness, overall shave quality and 5 hour closeness versus the control. In the second study (with humectant aftershave), the shave foam with cysteamine provided significant improvement in pull, glide, during shave comfort, and 5 hour closeness versus the control. The average ratings for pull and comfort in this study were two or more times better than the ratings for these attributes in the first study, where the humectant aftershave was not applied.

EXAMPLE 4

Non-soap self-foaming shave gel

| Ingredient | Wt. % |
| --- | --- |
| Water | 74.75 |
| Stearoyl/Myristoyl sarcosine | 7.11 |
| Oleth-20 | 4.33 |
| Isopentane Isobutane (3:1) | 3.85 |
| Myristyl alcohol | 2.69 |
| Triethanolamine (99%) | 2.60 |
| Mineral oil | 1.92 |
| Dimethethicone/dimethiconol | 0.19 |
| Hydroxyethyl cellulose | 0.24 |
| Polyquaternium-10 | 0.24 |
| PEG-14M | 0.14 |
| Fragrance/color/preserv. | q.s. |
| Cysteamine | 0.50 |

Procedure: Dissolve into the water at room temperature with stirring the hydroxyethyl cellulose, polyquaternium-10, and PEG-14M. After about 40 minutes of stirring, heat the aqueous solution to about 85° C., add the sarcosine (which has been pre-melted), myristyl alcohol, mineral oil and mix for about 10 minutes. Add the triethanolamine and Oleth-20 and continue mixing at about 85° C. for about 30 minutes. Cool to 70° C., add the preservative and mix for 10 minutes. Cool to 35° C. and add the cysteamine, silicone, fragrance, and colorant, then adjust the pH to 8.0–8.5. The mixture is purged with nitrogen gas to remove oxygen, cooled to room temperature, blended with the isopentane/isobutane and packaged in a barrier-type aerosol container.

This shave gel composition would be expected to provide improved pull, glide and comfort compared to an identical composition without the cysteamine.

EXAMPLE 5

Non-aerosol shave gel

| Ingredient | Wt. % |
| --- | --- |
| Water | 69.48 |
| Myristic acid | 10.40 |
| Palmitic acid | 5.15 |
| Potassium hydroxide | 3.62 |
| Oleth-20 | 3.00 |
| Sodium lauroyl sarcosinate | 2.25 |
| Sorbitol | 1.50 |
| Hydroxyethyl cellulose | 1.47 |
| PEG-150 distearate | 1.38 |
| Aloe/fragrance/color | q.s. |
| Cysteamine | 0.70 |

Procedure: Dissolve the hydroxyethyl cellulose into the water with stirring at room temperature, begin heating, add the sorbitol and continue heating to about 80° C. Add the fatty acids and PEG-150 distearate and mix until melted, then add the Oleth-20 slowly and mix until smooth and uniform. Add aqueous potassium hydroxide slowly and mix for about thirty minutes at about 85° C. until neutralization is complete. Begin cooling, then add the sarcosinate at about 65–70° C., the aloe at about 50° C., and the fragrance and colorant at about 40–45° C., then the cysteamine. The shaving gel (pH about 9.8) is packaged in a squeeze tube dispenser.

This shave gel composition was subjected to the cutting force analysis described in Example 1M, except that a water post-treatment was used in place of 25% glycerin (i.e. there was no humectant post-treatment). A 3–5% reduction in cutting force versus the control (Foamy/water) was demonstrated. This shave gel composition was also tested in a split face shave study with the control being an identical shave gel without cysteamine. No humectant aftershave was applied. In this study, the shave gel with cysteamine provided significant improvement in pull and during shave comfort versus the control and directional improvement in shave closeness, irritation and overall shave quality. Panelists also noted improved glide with the test composition.

While the invention has been described in detail with particular reference to preferred embodiments thereof, various modifications and substitutions will be apparent to those skilled in the art and should be considered to fall within the spirit and scope of the invention as defined by the following claims.

What is claimed is:

1. A shaving composition comprising about 65 to 90% water, about 5 to 25% of a water-soluble surface active foaming agent, and about 0.2 to 2.3% of cysteamine, said composition having a pH of about 8 to about 11.

2. The shaving composition of claim 1 comprising about 0.3 to about 1.5% of cysteamine.

3. The shaving composition of claim 2 having a pH of about 9 to 10.

4. The shaving composition of claim 1 comprising about 0.5 to about 1.0% of cysteamine and having a pH of about 9.3 to 9.8.

5. The shaving composition of claim 1, 2, 3 or 4 wherein said surface active foaming agent comprises a water-soluble soap, an anionic surfactant, a non-ionic surfactant, or a mixture thereof.

6. The shaving composition of claim 5 wherein said surface active foaming agent comprises a water-soluble soap which is selected from the group consisting of the sodium, potassium and/or lower alkanolamine salts of fatty acids, the sodium, potassium and/or lower alkanolamine salts of N-fatty acyl sarcosines, and mixtures thereof, wherein the fatty moiety has 10 to 20 carbon atoms.

7. The shaving composition of claim 6 wherein said water-soluble soap is selected from the group consisting of the sodium, potassium and/or lower alkanolamine salts of lauric acid, oleic acid, coconut oil acid, myristic acid, palmitic acid, stearic acid and mixtures thereof, and the sodium, potassium and/or lower alkanolamine salts of stearoyl sarcosine, myristoyl sarcosine, palmitoyl sarcosine, oleoyl sarcosine, lauroyl sarcosine, cocoyl sarcosine and mixtures thereof.

8. The shaving composition of claim 7 wherein said water-soluble soap is a triethanolamine salt of a fatty acid or an N-fatty acyl sarcosine or a mixture thereof.

9. The shaving composition of claim 1 in the form of an aerosol shaving foam additionally comprising about 1 to 5% of a volatile hydrocarbon propellant.

10. The shaving composition of claim 1 in the form of a self-foaming shaving gel additionally comprising a water-soluble gelling agent and about 1 to 8% of a volatile hydrocarbon self-foaming agent.

11. The shaving composition of claim 1 in the form of a non-aerosol, non-self-foaming shaving gel additionally comprising a water-soluble gelling agent.

12. The shaving composition of claim 9, 10 or 11 wherein said surface active foaming agent comprises a water-soluble soap, an anionic surfactant, a non-ionic surfactant, or a mixture thereof.

13. The shaving composition of claim 12 wherein said surface active foaming agent comprises a water-soluble soap which is selected from the group consisting of the sodium, potassium and/or lower alkanolamine salts of fatty acids, the sodium, potassium and/or lower alkanolamine salts of N-fatty acyl sarcosines, and mixtures thereof, wherein the fatty moiety has 10 to 20 carbon atoms.

14. A method of improving shaving comfort which comprises (a) contacting an area of hair to be shaved with the shaving composition of claim 1 and (b) shaving said area of hair.

15. The method of claim 14 additionally comprising (c) contacting said shaved area with a humectant and allowing it to dry.

16. The method of claim 15 additionally comprising repeating steps (a), (b) and (c).

* * * * *